United States Patent [19]
Surrey et al.

[11] 4,113,774
[45] Sep. 12, 1978

[54] N-(DICHLOROACETYL) DIAMINE COMPOUNDS AND PROCESS OF PREPARING SAME

[75] Inventors: Alexander R. Surrey, Albany; Joseph C. Collins, East Greenbush, both of N.Y.

[73] Assignee: Sterling Drug Inc., New York, N.Y.

[21] Appl. No.: 831,942

[22] Filed: Sep. 9, 1977

[51] Int. Cl.$^2$ .................. C07C 102/06; C07C 102/22
[52] U.S. Cl. .......................... 260/558 D; 260/561 HL
[58] Field of Search ...................... 260/558 D, 561 HL

[56] References Cited
U.S. PATENT DOCUMENTS

| | | | |
|---|---|---|---|
| 2,764,603 | 9/1956 | Ahlbrecht | 260/561 HL X |
| 3,677,739 | 7/1972 | Horrom et al. | 260/558 D X |

FOREIGN PATENT DOCUMENTS 787,400  12/1957  United Kingdom ............. 260/561 HL

OTHER PUBLICATIONS

Coulston, F. et al., "The Biologic Actions of a New Series of Bis(dichloroacetyl) Diamines, Toxicology and Applied Pharmacy, 2, 715–731 (1960).

*Primary Examiner*—Allen B. Curtis
*Attorney, Agent, or Firm*—Robert K. Bair; B. Woodrow Wyatt

[57] ABSTRACT

N-(Dichloroacetyl)-N'-(mono- or di-chlorobenzoyl)-1,8-octanediamines (I), acetaldehyde dehydrogenase inhibitors, indicating their usefulness as aids in treating alcoholism, are prepared by reacting a mono-acid-addition salt of 1,8-ocetanediamine with one molar equivalent quantity of a lower-alkyl dichloroacetate to produce N-(dichloroacetyl)-1,8-octanediamine and then reacting it with a mono- or di-chlorobenzoylating agent to produce I. Also shown is the process of reacting a mono-acid-addition salt of 1,6-hexanediamine with one molar equivalent quantity of a lower-alkyl dichloroacetate to produce N-(dichloroacetyl)-1,6-hexanediamine.

14 Claims, No Drawings

N-(DICHLOROACETYL) DIAMINE COMPOUNDS AND PROCESS OF PREPARING SAME

BACKGROUND OF THE INVENTION (a) Field of the Invention

This invention relates to unsymmetrical di-(acyl)-alkanediamine useful as acetaldehyde dehydrogenase inhibitors, to intermediates therefor and to processes for their preparation.

(b) Description of the Prior Art

N,N'-Bis(dichloroacetyl)-1,8-octanediamine, also known as Win 18,466, has been shown: (a) to have antispermatogenic activity in rats [F. Coulston, A. L. Beyler and H. P. Drobeck, Tox. and Appl. Pharmacology 2, 715-731 (1960)]; (b) to suppress spermatogenesis in man [C. G. Heller, D. J. Moore and C. A. Paulsen, Tox. and Appl. Pharmacology 3, 1-14 11 (1961]; (c) not to have in vivo amebicidal activity against E. criceti in hamsters [D. A. Berberian R. G. Slighter and A. R. Surrey, Antibiotics and Chemotherapy 11, 245-255 (1961)]; and, (d) to be an inhibitor of aldehyde dehydrogenase [R. A. Deitrich and L. Hellerman, J. Biol. Chem. 238, No. 5, 1683-1689 (May 1963)]. In discussing Win 18,466, Deitrich and Hellerman note that through their evaluation "results in a considerable underestimation of the effectiveness" of Win 18,466 and Win 13,099 [Win 13,099 is N,N'-bis(dichloroacetyl)-N,N'-diethyl-1,4-bis-(aminomethyl)benzene], "they appear to be about as effective as disulfiram", bis(diethylthiocarbamoyl) disulfide or ANTABUSE ®, an aid useful in treating alcoholism. Deitrich and Hellerman also report the following information about these two Win compounds: "One side effect of these compounds has been a reaction to ethanol in man and animals".

N,N'-Bis(benzoyl)-1,8-octanediamine was prepared by V. Prelog by reaction 1,8-octanediamine dihydrochloride with benzoyl chloride in aqueous potassium hydroxide solution [Helv. Chim. Acta 38, 1095 (1110) (1955)].

The SDI G. Y. Lesher U.S. Pat. No. 3,840,598, issued Oct. 8, 1974, discloses inter alia some unsymmetrical N,N'-diacyl-alkanediamines where "alkane" has from five to twelve carbon atoms, however, both "acyl" groups are 4-substituted benzoyl, at least one being 4-trifluoromethoxy(or the like)-benzoyl and the other being various 4-substituted-benzoyl groups, for example, 4-chloro-4'-trifluoromethoxy-N,N'-heptamethylenebis(benzamide). These compounds are disclosed as having antifertility activity, hypocholesteremic activity or adrenal hypertrophy activity. The intermediate N-(7-aminoheptyl)-4-(trifluoromethoxy)benzamide as its hydrochloride is prepared in Example 22 in two steps by first reacting 7-aminoheptanoitrile with 4-trifluoromethoxybenozyl fluoride in chloroform and aqueous sodium hydoxide solution and catalytically hydrogenating in the presence of ammonia and Raney nickel the resulting N-(6-cyanohexyl)-4-trifluoromethoxybenzamide to produce said corresponding N-(7-aminoheptyl) compound. The following N,N'-bis(3,5-dihalosalicyloyl)alkanediamines were shown to have in vitro antibacterial activity [Jerchel et al., Ann. d. Chemie 590, 242-248 (1954)]:

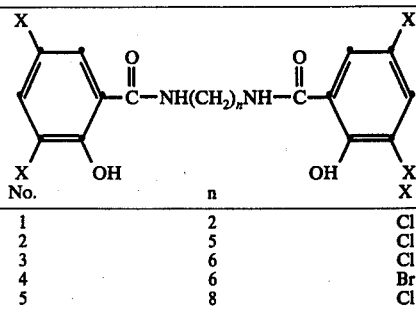

| No. | n | X |
|---|---|---|
| 1 | 2 | Cl |
| 2 | 5 | Cl |
| 3 | 6 | Cl |
| 4 | 6 | Br |
| 5 | 8 | Cl |

SUMMARY OF THE INVENTION

In one composition aspect, the invention relates to N-(dichloroacetyl)-N'-(mono- or di-chlorobenzoyl)-1,8-octanediamine (I), which are acetaldehyde dehydrogenase inhibitors, thereby indicating their usefulness as aids in treating alcoholism. Preferred embodiments are N-(dichloroacetyl)-N'-(4-chlorobenzoyl)-1,8-octanediamine and N-(dichloroacetyl)-N'-(3,4-dichlorobenzoyl)-1,8-octanediamine.

In another composition aspect, the invention relates to N-(dichloroacetyl)-1,8-octanediamine or N-(dichloroacetyl)-1,6-hexanediamine, which are useful as intermediates.

The invention in a process aspect comprises reacting a mono-acid-addition salt of 1,8-octanediamine with one molar equivalent of a lower-alkyl dichloroacetate to produce N-(dichloroacetyl)-1,8-octanediamine and then reacting it with one molar equivalent of a mono-chlorobenzoylating or dichlorobenzoylating agent to produce N-(dichloroacetyl)-N'-(mono- or di-chlorobenzoyl)-1,8-octanediamine.

The invention in another process aspect comprises reacting a mono-acid-addition salt of 1,8-octanediamine or 1,6-hexanediamine with one molar equivalent of a lower-alkyl dichloroacetate to produce N-(dichloroacetyl) -1,8-octanediamine or N-(dichloroacetyl)-1,6-hexanediamine.

DETAILED DESCRIPTION INCLUSIVE OF PREFERRED EMBODIMENTS

The invention in a composition aspect resides in a compound having the formula

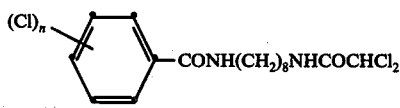

where $n$ is 1 or 2.

The compounds of formula I are useful to inhibit acetaldehyde dehydrogenase, as determined by proven biological evaluation procedures, and are acetaldehyde dehydrogenase inhibitors thereby indicating their usefulness as acids in treating alcoholism. Unlike the highly antispermatogenically-active N,N'-bis)(dichloroacetyl)-1,8-octanediamine [Coulston et al., supra, and Surrey U.S. Pat. No. 3,143,566, issued Aug. 4, 1964], our compounds of formula I surprisingly were found to have no antispermatogenic activity.

The invention in another composition aspect resides in the compound having the formula II

II where n is 6 or 8 or acid-addition salt thereof. The compound of formula II where n is 8 is useful in the preparation of the compounds of formula I described above. The compound of formula II where n is 6 was useful as an intermediate in a model experiment using the relatively inexpensive 1,6-hexanediamine to devise a process for preparing N-(dichloroacetyl)-1,6-hexanediamine, said process then applied to the more expensive 1,8-octanediamine.

The invention in a process aspect comprises reacting a mono-acid-addition salt of 1,8-octanediamine with one molar equivalent quantity of a lower-alkyl dichloroacetate to produce N-(dichloroacetyl)-1,8-octanediamine and reacting it with a mono- or di-chlorobenzoylating agent to produce the compound of formula I above. This process is preferably carried out using 4-chlorobenzoyl or 3,4-dichlorobenzoyl chloride and methyl dichloroacetate.

The invention in another process aspect comprises reacting a mono-acid-addition salt of 1,6-hexanediamine or 1,8-octadiamine with one molar equivalent quantity of a lower-alkyl dichloroacetate to produce N-(dichloroacetyl)-1,6-hexanediamine or N-(dichloroacetyl)-1,8-octanediamine. This process is carried out preferably using methyl dichloroacetate.

The compounds of formula II are useful both in the free base form and in the form of acid-addition salts; and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts. In practicing the invention, it was found convenient to use the phosphate salts; however, other appropriate pharmaceutically acceptable salts within the scope of the invention are those derived from mineral acids such as hydrochloric acid, sulfuric acid and sulfamic acid; and organic acids such as acetic acid, citric acid, tartaric acid, lactic acid, methanesulfonic acid, ethanesulfonic acid, benzenesulfonic acid, p-toluenesulfonic acid, quinic acid, cyclohexylsulfamic acid, and the like giving the hydrochloride, sulfate, sulfamate, acetate, citrate, tartrate, lactate, methanesulfonate, ethanesulfonate, benzenesulfonate, p-toluenesulfonate, quinate and cyclohexylsulfamate, respectively.

The acid-addition salt of said basic compounds are prepared either by dissolving the free base in aqueous or aqueous-alcohol solution containing the appropriate acid and isolating the salt by evaporating the solution, or by reacting the free base and acid in an organic solvent, in which case the salt separates directly or can be obtained by concentration of the solution.

The molecular structures of the composition aspects I and II of the invention were assigned on the basis of evidence provided by infrared, ultraviolet, nuclear magnetic resonance and mass spectra, by chromatographic mobilities, and, by the correspondence of calculated and found values for the elementary analyses for representative examples.

The manner of making and using the instant invention will now be generally described so as to enable a person skilled in the art of pharmaceutical chemistry to make and use the same, as follows:

The preparation of the compounds of formula II is carried out under anhydrous conditions by reacting in an inert medium, preferably an lower-alkanol or mixture thereof, e.g., methanol, ethanol, and the like, a mono-acid-addition salt, preferably hydrochloride, of 1,6-hexanediamine or 1,8-octanediamine, with one molar equivalent of a lower-alkyl dichloroacetate, preferably methyl or ethyl dichloroacetate. The reactants are preferably mixed at about 0° to 5° C. and then heated at about 50 to 80° C. Other inert solvents can be used, e.g., isopropyl alcohol, tetrahydrofuran, dioxane, dichloromethane, dimethylformamide, and the like. Since some diacylation occurs to produce N,N'-bis(dichloroacetyl)-1,6-hexanediamine or N,N'-bis(dichloroacetyl)-1,8-octanediamine, the water-insoluble diacylated-diamine is readily removed by adding water to the reaction mixture, mixing well and filtering off the diacylated-diamine. The monoacylated product as its acid-addition salt remains in the filtrate and is readily obtained by treating the filtrate with an appropriate alkaline agent, e.g., potassium or sodium carbonate, potassium or sodium hydroxide, and the like, and extracting the monoacylated compound in free base form with a suitable solvent, e.g., ether, chloroform, methylene dichloride, benzene and the like. Evaporation of the solvent yields the monoacylated compound.

Prior to the carrying out of the above-described process for preparing II by reaction of the mono-acid-addition salt of 1,6-hexanediamine or 1,8-octanediamine with one molar equivalent of a lower-alkyl dichloroacetate, no less than seven different methods had been unsuccessfully attempted to prepare N-(dicloroacetyl)-1,6-hexanediamine or N-(dichloroacetyl)-1,8-octanediamine.

The preparation of the compounds of formula I is carried out by reacting N-(dicloroacetyl)-1,8-octanediamine with a mono- or di-chlorobenzoylating agent, preferably mono- or di-chlorobenzoyl halide in the presence of an acid-acceptor. The reaction is carried out preferably by stirring the reactants kept at about 0° to 5° C. in a medium consisting of water and a suitable water-immiscible solvent inert under the reaction conditions, e.g., ethylene dichloride, methylene dichloride, chloroform, benzene, and the like, and then preferably allowing the reaction mixture to warm up to room temperature and to stand a short period to ensure completion of the reaction. An acid-acceptor as used above is a basic substance capable of neutralizing the hydrogen halide formed by the reaction (when a mono- or di-chlorobenzoyl halide is used), e.g., an alkali hydroxide, preferably sodium or potassium hydroxide, an alkali carbonate, preferably potassium or sodium carbonate.

Alternatively, other available benzoylating agents can be used in place of said benzoyl halides in the process of the invention. For example, the reaction can be carried out by heating a lower-alkyl mono- or di-chlorobenzoate with N-(dichloroacetyl)-1,8-octanediamine or by reacting mono- or di-chlorobenzoic anhydride with N-(dichloroacetyl)-1,8-octanediamine to form the final product of formula I. Also, the product of I can be obtained by heating N-(dichloroacetyl)-1,8-octanediamine with mono- or di-chlorobenzoic acid either in the absence or presence of a suitable solvent, for example, dimethylformamide, ethylene dichloride, benzene, tetrahydrofuran, and the like, and either in the absence or presence of a dehydrating or activating agent, e.g., dicyclohexylcarbodiimide, 1,1-carbonyldimidazole, and the like.

The following experiments will further illustrate the invention without, however, limiting it thereto.

A. N-(DICHLOROACETYL)-ALKANEDIAMINES

A-1. N-(Dichloroacetyl)-1,6-hexanediamine

To a cooled solution containing 29 g. of 1,6-hexanediamine, 55.5 ml. of 4.5N hydrogen chloride in absolute ethanol and 500 ml. of absolute methanol was added with swirling 39 g. of methyl dichloroacetate. The solution was refluxed for one hour and then evaporated to dryness under reduced pressure. The residue was taken up with 500 ml. of water and the insoluble material was collected and washed with 100 ml. of water. There was thus obtained 19 g. (45% yield) of N,N'-bis(dichloroacetyl)-1,6-hexanediamine. The above aqueous filtrate combined with the aqueous washings was made alkaline with 50 g. of anhydrous potassium carbonate and the basic mixture was continuously extracted with 1 liter of ether for two hours and the ether extract was allowed to stand overnight. The ether extract was evaporated in vacuo to yield, as a pale yellow liquid, 9.5 g. of N-(dichloroacetyl)-1,6-hexanediamine, which was dissolved in 100 ml. of isopropyl alcohol and treated with 53 ml. of 1.0M phoshoric acid in absolute ethanol with swirling and then cooling. The resulting suspension was diluted with an equal volume of ether and the solid collected by filtration. This product was combined with another sample obtained by treating 4.6 g. of N-(dichloroacetyl)-1,6-hexanediamine in 50 ml. of absolute ethanol with 26 ml. of 1M phosphoric acid and the combined materials were recrystallized from methanol-ether, and dried for three days at 80° C. and 15mm. to yield 16 g. of white solid. This solid was then recrystallized again from methanol-ether and once from absolute ethanol, dried at 70° C. and 15mm. for 20 hours to yield 12 g of N-(dichloroacetyl)-1,6-hexanediamine phosphate, m.p. 155.2°–158.2° C. (corr.). Further continuous ether extraction of the original aqueous solution [after removal of the bis(dichloroacetyl) derivative] provided an additional .9 g. of N-(dichloroacetyl)-1,6-hexanediamine as an oil.

A-2. N-(Dichloroacetyl)-1,8-octanediamine

To an ice-cooled solution containing 116 g. of 1,8-octanediamine in 1500 ml. of absolute methanol was added 91 ml. of 8.8N hydrogen chloride in ethanol, followed by 100 g. of methyl dichloroacetate with stirring over a thirty-minute period. The resulting mixture was refluxed for two hours and then evaporated in vacuo to yield a solid. The solid was shaken well with 2000 ml. of water and the insoluble N,N'-bis(dichloroacetyl)-1,8-octanediamine was collected and washed with a small quantity of water. The combined aqueous filtrate and washings were made basic with 110.6 g. of potassium carbonate and the alkaline mixture was extracted continuously for six hours with ether. The ether extracts were combined, dried over anhydrous magnesium sulfate and evaporated in vacuo to yield, as a yellow oil, 64.8 g. of N-(dichloroacetyl)-1,8-octanediamine, portions of which were used in Examples B-1 and B-2. To a solution containing 15.2 g. of N-(dichloroacetyl)-1,8-octanediamine in 200 ml. of isopropyl alcohol was added with stirring 60 ml. of 1N phosphoric acid in ethanol. The mixture was swirled and allowed to stand overnight. The solid was collected, recrystallized from ethanol and dried in vacuo (15mm.) at 30° C. for fifteen hours to yield 7.9 g. of N-(dichloroacetyl)-1,8-alkanediamine phosphate, m.p. 117.4-(indef.)

B. N-(DICHLOROACETYL)-N'-(MONO- OR DI-CHLOROBENZOYL)-1,8-OCTANEDIAMINES

B-1. N-(Dichoroacetyl)-N'-(4-chlorobenzoyl)-1,8-octanediamine

To a cold mixture containing 12.8 g. of N-(dichloroacetyl)-1,8-octanediamine in 200 ml. of ethylene dichloride mixed with 2.0 g. of sodium hydroxide in 50 ml. of water kept at about 5° C. was added dropwise with stirring 8.8 g. of 4-chlorobenzoyl chloride. After about thirty minutes, stirring was discontinued and after two hours the reaction mixture was filtered and the collected solid was recrystallized from isopropyl alcohol and dried at 25mm. and 55° C. for 60 hours to yield 7.5 g. of the product, N-(dichloroacetyl)-N'-(4-chlorobenzoyl)-1,8-octanediamine, m.p. 140.0°–142.2° C. (corr.).

B-2. N-(Dichloroacetyl)-N'-(3,4-dichlorobenzoyl)-1,8-octanediamine

To a chilled mixture containing 12.8 g. of N-(dichloroacetyl)-1,8-octanediamine in 200 ml. of ethylene dichloride and 2.0 g. of sodium hydroxide in 50 ml. of water was added dropwise with vigorous stirring, keeping the reaction mixture at about 5° C., 10.5 g. of 3,4-dichlorobenzoyl chloride. The reaction mixture was stirred for about thirty minutes, allowed to stand for 1 hour and then the solid product was collected by filtering the mixture. The solid was recrystallized twice from isopropyl alcohol and dried at 55° C. and 25mm. for 60 hours to yield 6.8 g. of N-(dichloroacetyl)-N'-(3,4-dichlorobenzoyl)-1,8-octanediamine, m.p. 116.4°–133.4° C. (corr.).

It is contemplated that following the procedure described in Example B-1 using in place of 4-chlorobenzoyl chloride a molar equivalent quantity of the appropriate chlorobenzoyl chloride, there will be obtained the following respective N-(dichloroacetyl)-N'-(monochlorobenzoyl)-1,8-octanediamines of Examples B-3 and B-4.

B-3. N-(Dichloroacetyl)-N'-(3-chlorobenzoyl)-1,8-octanediamine using 3-chlorobenzoyl chloride.

B-4. N-(Dichloroacetyl)-N'-(2-chlorobenzoyl)-1,8-octanediamine using 2-chlorobenzoyl chloride.

It is contemplated that following the procedure described in Example B-2 using in place of 3,4-dichlorobenzoyl chloride a molar equivalent quantity of the appropriate dichlorobenzoyl chloride, there will be obtained the following respective compounds of Examples B-5 through B-7.

B-5. N-(Dichloroacetyl)-N'-(2,4-dichlorobenzoyl)-1,8-octadiamine using 2,4-dichlorobenzoyl chloride.

B-6. N-(Dichloroacetyl)-N'-(3,5-dichlorobenzoyl)-1,8-octanediamine using 3,5-dichlorobenzoyl chloride.

B-7. N-(Dichloroacetyl)-N'-(2,6-dichlorobenzoyl)-1,8-octanediamine using 2,6-dichlorobenzoyl chloride.

The usefulness of the compounds of formula I is demonstrated by their effectiveness in proven biological test procedures, for example, by establishing their high inhibitory action (greater than that of disulfiram) against liver acetaldehyde dehydrogenase according to the following proven test procedure: Liver aldehyde dehydrogenase was prepared from freshly excised bovine liver by the method of Deitrich et al. [J. Biol. Chem. 237, 560 (1962)]. The specific activity of the partially purified enzyme preparation was 172 units per milligram of protein. The assay system contained 30μ moles of sodium pyrophosphate buffer with a final pH of 9.6, 135μ moles of propylene glycol to serve as a vehicle for the compound being tested, 0.5μ mole of propionaldehyde, 1μ mole of nicotinamide adenine dinucleotide and 120 units of enzyme to initiate the reaction in a total volume of 3.0 milliliters. The assay mixture was contained in 1 centimeter silica cuvettes. The reaction was followed by measuring the increase in optical density at 340 mμ with time on the Beckman du spectrophotometer which was equipped with dual thermospacers set to maintain the temperature of the cell compartment at 26.0 ± 0.1° C. by means of a circulating water bath (Haake Thermostat F, Berlin). Readings of optical density were taken each minute for 15 minutes. The optical density at 15 minutes corrected for optical density at zero time was used to calculate percent inhibition compared with controls which contained all constituents except the compound being tested. Fifty percent inhibition values ($I_{50}$) were determined from first order reaction plots at multiple levels of the tested compound. Sodium pyrophosphate changes pH when diluted with the other reaction constitutents in water; so, this effect was compensated for to bring the final pH of the incubation mixture to 9.6.

When tested by the above-described procedure, Examples B-1 and B-2 (supra) and disulfiram were found to have the following respective $I_{50}$ values (molar concentration for 50% inhibition) for inhibition of liver acetaldehyde dehydrogenase: $2.7 \times 10^{-6}M$, $8.2 \times 10^{-7}M$ and $1.3 \times 10^{-5}M$.

The compounds of formula I can be prepared for use by conventional pharmaceutical procedures: that is, by dissolving or suspending them in a pharmaceutically acceptable, e.g., aqueous alcohol, glycol, oil solution, or oil-water emulsion, for oral or parenteral administration; or by incorporating them in unit dosage form as tablets or capsules for oral administration either alone or in combination with conventional adjuvants, e.g., calcium carbonate, starch, lactose, talc, magnesium stearate, gum acacia, and the like.

We claim:

1. A compound having the formula

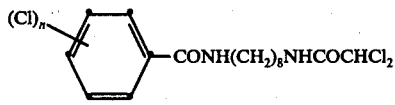

where n is 1 or 2.

2. N-(Dichloroacetyl)-N'-(monochlorobenzoyl)-1,8-octanediamine according to claim 1 where n is 1.

3. N-(Dichloroacetyl)-N'-(dichlorobenzoyl)-1,8-octanediamine according to claim 1 where n is 2.

4. N-(Dichloroacetyl)-N'-(4-chlorobenzoyl)-1,8-octanediamine.

5. N-(Dichloroacetyl)-N'-(3,4-dichlorobenzoyl)-1,8-octanediamine.

6. The process for preparing the compound of claim 1 which comprises reacting a mono-acid-addition salt of 1,8-octanediamine with one molar equivalent of a lower-alkyl dichloroacetate to produce N-(dichloroacetyl)-1,8-octanediamine and then reacting it with one molar equivalent of a monochloroenzoylating or dichlorobenzoylating agent to produce said compound of claim 1.

7. The process according to claim 6 which comprises reacting 1,8-octanediamine monohydrochloride with one molar equivalent of methyl dichloroacetate and then reacting the resulting N-(dichloroacetyl)-1,8-octanediamine with one molar equivalent of 4-chlorobenzoyl chloride to produce the compound of claim 4.

8. The process according to claim 6 which comprises reacting 1,8-octanediamine monohydrochloride with one molar equivalent of methyl dichloroacetate and reacting the resulting N-(dichloroacetyl)-1,8-octanediamine with 3,4-dichlorobenzoyl chloride to produce the compound of claim 5.

9. A compound having the formula $$H_2N(CH_2)_nNHCOCHCl_2$$

where n is 6 or 8, or acid-addition salt thereof.

10. N-(Dichloroacetyl)-1,8-octanediamine according to claim 9 where n is 8.

11. N-(Dichloroacetyl)-1,6-hexanediamine according to claim 9 where n is 6.

12. The process for preparing the compound of claim 9 which comprises reacting a mono-acid-addition salt of 1,6-hexanediamine or 1,8-octanediamine with one molar equivalent quantity of a lower-alkyl dichloroacetate to produce N-(dichloroacetyl)-1,6-hexanediamine or N-(dichloroacetyl)-1,8-octanediamine.

13. The process according to claim 12 which comprises reacting a mono-acid-addition salt of 1,6-hexanediamine with one molar equivalent quantity of methyl dichloroacetate to produce N-(dichloroacetyl)-1,6-hexanediamine.

14. The process according to claim 12 which comprises reacting a mono-acid-addition salt of 1,8-octanediamine with one molar equivalent quantity of methyl dichloroacetate to produce N-(dichloroacetyl)-1,8-octanediamine.

UNITED STATES PATENT AND TRADEMARK OFFICE
CERTIFICATE OF CORRECTION

PATENT NO. : 4,113,774

DATED : September 12, 1978

INVENTOR(S) : Alexander R. Surrey and Joseph C. Collins

It is certified that error appears in the above-identified patent and that said Letters Patent are hereby corrected as shown below:

Title page, ABSTRACT [57], line 5, "ocetanediamine" should read -- octanediamine --.

Column 1, line 19, "1-14 11" should read -- 1-11 --.

Column 1, line 58, "7-aminoheptanoitrile" should read -- 7-aminoheptanonitrile --.

Column 1, line 59, "fluoromethoxybenozyl" should read -- fluoromethoxybenzoyl --.

Column 1, line 60, "hydoxide" should read -- hydroxide --.

Column 1, line 65, a new paragraph should start beginning with "The following".

UNITED STATES PATENT AND TRADEMARK OFFICE
CERTIFICATE OF CORRECTION

PATENT NO. : 4,113,774

DATED : September 12, 1978

INVENTOR(S) : Alexander R. Surrey and Joseph C. Collins

It is certified that error appears in the above-identified patent and that said Letters Patent are hereby corrected as shown below:

Column 2, line 61, "N,N'-bis) (..." should read -- N,N'-bis(... --.

Column 3, line 21, "1,8-octadiamine" should read --1,8-octanediamine --.

Column 3, line 48, "salt" should read -- salts --.

Column 4, line 30, "(dicloroacetyl)" should read -- (dichloroacetyl) --.

Column 4, line 34, "(dicloroacetyl)" should read -- (dichloroacetyl) --.

Column 4, line 65, "1,1-carbonyldim-", should read --1,1-carbonyldi- --; and line 66, "midazole" should read -- imidazole --.

Column 8, line 15, "monochloroenzoylating" should read -- monochlorobenzoylating --.

Signed and Sealed this

Twenty-second Day of May 1979

[SEAL]

Attest:

RUTH C. MASON
Attesting Officer

DONALD W. BANNER
Commissioner of Patents and Trademark